(12) United States Patent
Cramer et al.

(10) Patent No.: US 10,475,352 B2
(45) Date of Patent: Nov. 12, 2019

(54) SYSTEMS AND METHODS FOR FACILITATING REHABILITATION THERAPY

(71) Applicant: The Regents of the University of California, Oakland, CA (US)

(72) Inventors: Steven C. Cramer, Irvine, CA (US); Jessica M. Cassidy, Huntington Beach, CA (US); Vu Le, Irvine, CA (US); Alison L. McKenzie, Capistrano Beach, CA (US); Walt Scacchi, Corona Del Mar, CA (US); Robert Zhou, Monterey Park, CA (US); Jutta Heckhausen, Irvine, CA (US); William F. Genevro, Oakland, CA (US); Lucy Dodakian, Oakland, CA (US); Jill See, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 108 days.

(21) Appl. No.: 15/254,029

(22) Filed: Sep. 1, 2016

(65) Prior Publication Data
US 2017/0069223 A1    Mar. 9, 2017

Related U.S. Application Data

(60) Provisional application No. 62/216,177, filed on Sep. 9, 2015.

(51) Int. Cl.
*G09B 19/00*  (2006.01)
*G09B 5/06*   (2006.01)
(Continued)

(52) U.S. Cl.
CPC .............. *G09B 19/003* (2013.01); *A61B 5/11* (2013.01); *A63B 23/14* (2013.01); *A63B 23/16* (2013.01);
(Continued)

(58) Field of Classification Search
CPC ............. G06F 19/3481; G06F 19/3418; A61B 5/1118; A61B 5/11; A61B 2505/09;
(Continued)

(56) References Cited

U.S. PATENT DOCUMENTS 9,311,789 B1 * 4/2016 Gwin ..................... G08C 19/00
9,724,598 B2 * 8/2017 Burdea ................... A63F 13/06
(Continued)

*Primary Examiner* — Jack Yip
(74) *Attorney, Agent, or Firm* — Nguyen Tarbet

(57) ABSTRACT

A rehabilitation system includes a portable patient workstation configured to facilitate in-home rehabilitation therapy. In some embodiments, the workstation includes a computer configured to host computer-based activities that provide rehabilitative exercise to a patient when the patient participates in the activities, a monitor electrically connected to the computer and configured to display screens of the computer-based activities, a table upon which the monitor can be supported, a tabletop console supported on the table, the console including multiple integral user interface devices that are connected to the computer and adapted to receive patient inputs while the patient is participating in the activities, and a network interface device with which data can be transmitted and received by the patient workstation via a network.

20 Claims, 17 Drawing Sheets

(51) Int. Cl.

| | |
|---|---|
| *G07F 17/32* | (2006.01) |
| *A61B 5/11* | (2006.01) |
| *A63B 71/06* | (2006.01) |
| *A63B 23/14* | (2006.01) |
| *A63B 23/16* | (2006.01) |
| *A63F 13/428* | (2014.01) |
| *A63F 13/24* | (2014.01) |
| *A63F 13/213* | (2014.01) |
| *A63F 13/218* | (2014.01) |
| *G16H 40/63* | (2018.01) |
| *G16H 20/30* | (2018.01) |
| *A63B 23/12* | (2006.01) |
| *A63B 22/00* | (2006.01) |
| *A63B 21/00* | (2006.01) |

(52) U.S. Cl.
CPC ........ *A63B 71/0622* (2013.01); *A63F 13/213* (2014.09); *A63F 13/218* (2014.09); *A63F 13/24* (2014.09); *A63F 13/428* (2014.09); *G07F 17/32* (2013.01); *G09B 5/06* (2013.01); *G16H 20/30* (2018.01); *G16H 40/63* (2018.01); *A61B 5/1118* (2013.01); *A61B 2505/09* (2013.01); *A63B 21/4035* (2015.10); *A63B 23/1209* (2013.01); *A63B 2022/0094* (2013.01); *A63B 2071/063* (2013.01); *A63B 2071/0625* (2013.01); *A63B 2071/0638* (2013.01); *A63B 2071/0658* (2013.01); *A63B 2207/02* (2013.01); *A63B 2220/51* (2013.01); *A63B 2220/803* (2013.01); *A63B 2220/807* (2013.01); *G09B 19/0038* (2013.01)

(58) Field of Classification Search
CPC .... G09B 19/0038; G09B 19/003; G09B 5/06; A63F 13/213; A63F 13/218; A63F 13/24; A63F 13/428; G16H 20/30; G16H 40/63; A63B 23/14; A63B 23/16; A63B 71/0622; A63B 21/4035; A63B 23/1209; A63B 2022/0094; A63B 2071/0625; A63B 2071/063; A63B 2071/0638; A63B 2071/0658; A63B 2207/02; A63B 2220/51; A63B 2220/803; A63B 24/0062; A63B 2220/807; G07F 17/32
USPC ........................................................ 434/247
See application file for complete search history.

(56) References Cited

U.S. PATENT DOCUMENTS

| | | | |
|---|---|---|---|
| 2005/0065452 A1* | 3/2005 | Thompson | A61B 5/162 600/558 |
| 2006/0287617 A1* | 12/2006 | Taub | A61H 1/02 601/24 |
| 2007/0060445 A1* | 3/2007 | Reinkensmeyer | A61H 1/0274 482/1 |
| 2007/0282228 A1* | 12/2007 | Einav | A63B 21/4021 601/33 |
| 2013/0143718 A1* | 6/2013 | Pani | A63B 21/0004 482/8 |
| 2014/0074180 A1* | 3/2014 | Heldman | A61B 5/1101 607/45 |
| 2014/0121018 A1* | 5/2014 | Burdea | A63F 13/06 463/36 |
| 2015/0004581 A1* | 1/2015 | Selman | G06K 9/00342 434/257 |
| 2017/0337834 A1* | 11/2017 | Shindi | G09B 5/02 |
| 2017/0361217 A1* | 12/2017 | Burdea | A63F 13/06 |

* cited by examiner

FIG. 6

UC IRVINE TELEREHABILITATION STROKE STUDY

Return

Subject ID: dovj
Assessed by: MI
Reflex biceps 2
Reflex triceps 2
Shoulder girdle reaction 2
Shoulder girdle elevation 2
Shoulder abduction 1
Shoulder external rotation 2
Elbow flexion 2
Forearm supination 1
Shoulder aduction/internal roation 2
Elbow extension 1
Forearm pronation 1
Hand to lumbar spine 2
Shoulder flexion, 0.90 2
Pronation supiration forearm, elbow flexed 1
Shoulder abduction 0.90 1

FIG. 7A

UC IRVINE TELEREHABILITATION STROKE STUDY

Back to Subject List | Main Menu

Choose An Activity
- ▷ Decreased proximal strength
- ▷ Decreased detail strength
- ▽ Decreased grip strength
  - ▷ Exercises
  - ▽ Games
    - Flappy Bird
    - Targeting
- ▷ Decreased pinch strength
- ▷ Decreased prox motor control
- ▷ Decreased detail motor control
- ▷ Decreased fine motor control
- ▷ Other VuTest (TR Group)
Supervised Session #1
10/5/2015

Start Time: 10:00am

Video Chat-Review (10/10 minutes)
→ Video Chat  ×

Exercises (10/10 minutes)
→ 3 Transfer Object (73)  ×
→ B Shldr Horiz Abd w/Tubing (99)  ×
→ B/oc Elbow Flexion (52)  ×

Games (10/10 minutes)
→ Bubble Bop  ×
→ Cut the Rope  ×

Anything (10/10 minutes)
→ All Finger Ext (35)  ×
→ Targeting  ×

Break (10/10 minutes)

Current Itinerary for VuTest
Uploaded
Total time: 80 Minutes

- Video Chat 10 minutes

- 3 Transfer Object (73) 2 minutes
- B Shldr Horiz Abd w/Tubing (99) 3 minutes
- B/oc Elbow Flexion (52) 5 minutes

- Bubble Bop 5 minutes (PS Move)
- Cut the Rope 5 minutes (PS Move)

- All Finger Ext (33) 5 minutes
- Targeting 5 minutes (Squeeze)

- Rest 10 minutes

- Finger MF Ext Stretch (37) 5 minutes
- MP Ext 10 Flex (56) 5 minutes
- Flappy Bird 10 minutes (Button)
- Button Presses 5 minutes (Buttons)
- DIP Extension Strength (56) 5 minutes Copy to...
Email To...
Upload Transfer Object Grasp and hold object with one hand. Transfer object to other hand. Reverse. Use objects of different shapes, sizes and weight.

Remaining Time: 179

| Task ID | Date | Assigned Itinerary Name | Received Score? | Task ID | Date | Completed Actions Name | Transmitted Score |
|---|---|---|---|---|---|---|---|
| 200595 | 8/23/2016 | Stroke Education | True | 200595 | 09:40:55 | Stroke Education | 13000 |
| 200596 | 8/23/2016 | Exercise-Shoulder Circles | True | 200596 | 09:41:01 | Exercise-Shoulder Circles | 0 |
| 200597 | 8/23/2016 | Exercise-Shldr Dep w/Tubing | True | 200597 | 09:44:10 | Exercise-Shldr Dep w/Tubing | 0 |
| 200598 | 8/23/2016 | Exercise-Elbow Ext w/Tubing | True | 200598 | 09:46:17 | Exercise-Elbow Ext w/Tubing | 0 |
| 200599 | 8/23/2016 | Exercise-Hold & Stretch Wrist Ext | True | 200599 | 09:47:33 | Exercise-Hold & Stretch Wrist Ext | 0 |
| 200600 | 8/23/2016 | Exercise-Resisted Finger Flex | True | 200600 | 09:49:40 | Exercise-Resisted Finger Flex | 0 |
| 200601 | 8/23/2016 | Exercise-Finger Flexor Stretch | True | 200601 | 09:51:47 | Exercise-Finger Flexor Stretch | 0 |
| 200602 | 8/23/2016 | Game-Water Race | True | 200602 | 09:53:54 | Game-Water Race | 16 |
| 200603 | 8/23/2016 | Game-Tempest | True | 200603 | 09:55:10 | Game-Tempest | 3000 |
| 200604 | 8/23/2016 | Game-Targeting | True | 200604 | 09:59:33 | Game-Targeting | 134 |
| 200605 | 8/23/2016 | Game-Space Invaders | True | 200605 | 10:01:46 | Game-Space Invaders | 136 |
| 200606 | 8/23/2016 | Game-Reaction Time | True | 200606 | 10:04:56 | Game-Reaction Time | 1237.8571428571 |
| 200607 | 8/23/2016 | Game-Jewel Match | True | 200607 | 10:08:05 | Game-Jewel Match | 2400 |
| 200608 | 8/23/2016 | Game-Poker | True | 200608 | 10:13:16 | Game-Poker | 0 |
| 200609 | 8/23/2016 | Game-Flappy Bird | True | 200609 | 10:15:41 | Game-Flappy Bird | 12 |
| 200610 | 8/23/2016 | Game-Drums | True | 200610 | 10:18:53 | Game-Drums | 1700 |
| 200611 | 8/23/2016 | Break | True | 200611 | 10:29:08 | Break | 0 |
| 200612 | 8/23/2016 | Game-Duck Hunt | True | 200612 | 15:55:42 | Game-Duck Hunt | 16 |
| 200613 | 8/23/2016 | Game-Driving | True | 200613 | 15:59:10 | Game-Driving | 13 |
| 200614 | 8/23/2016 | Game-Button Presses | True | 200614 | 16:01:20 | Game-Button Presses | 5600 |
| 200615 | 8/23/2016 | Game-Blackjack | True | 200615 | 16:06:30 | Game-Blackjack | 0 |
| 200616 | 8/23/2016 | Game-Carnival Shooting | True | 200616 | 16:08:43 | Game-Carnival Shooting | 3100 |
| 200617 | 8/23/2016 | Game-Memory | True | 200617 | 16:11:51 | Game-Memory | 900 |
| 200618 | 8/23/2016 | Game-Piano | True | 200618 | 16:14:03 | Game-Piano | 1200 |
| 200619 | 8/23/2016 | Game-Range of Motion | True | 200619 | 16:16:12 | Game-Range of Motion | 1 |
| 200620 | 8/23/2016 | Game-Poker | True | 200620 | 16:21:50 | Game-Poker | 0 |
| 200621 | 8/23/2016 | Exercise-Trunk Rotation | True | 200621 | 16:23:59 | Exercise-Trunk Rotation | 0 |
| 200622 | 8/23/2016 | Exercise-Shoulder Shrug | True | 200622 | 16:25:10 | Exercise-Shoulder Shrug | 0 |
| 200623 | 8/23/2016 | Exercise-Shoulder Posterior Capsule | True | 200623 | 16:27:18 | Exercise-Shoulder Posterior Capsule | 0 |

Last Data Retrieved 5:00AM PST, Wednesday August 24, 2016

SYSTEMS AND METHODS FOR FACILITATING REHABILITATION THERAPY

CROSS-REFERENCE TO RELATED APPLICATION

This application claims priority to U.S. Provisional Application Ser. No. 62/216,177, filed Sep. 9, 2015, which is hereby incorporated by reference herein in its entirety.

NOTICE OF GOVERNMENT-SPONSORED RESEARCH

This invention was made with Government support under Grant No. NS091951, awarded by the National Institutes of Health. The Government has certain rights in the invention.

BACKGROUND

Studies show that patients with a neurological injury, such as due to stroke, multiple sclerosis, trauma, or a degenerative brain condition such as amyotrophic lateral sclerosis, benefit from treatment by a clinician, such as a physical therapist, specializing in rehabilitation therapy combined with home exercising. Unfortunately, most people only receive limited amounts of therapy and similarly perform only limited amounts of home exercise. The reasons for this can include the high cost of and limited access to rehabilitation therapy and low motivation to perform exercises at home. Regardless of the reasons, the limited amounts of rehabilitation therapy provided and home exercising performed often result in the patient not achieving the highest level of recovery. In view of this, it can be appreciated that it would be desirable to have a means with which rehabilitation therapy can be made more accessible to patients at a lower cost and at the same time to enhance patients' motivation to perform exercises at home on a daily and long-term sustainable basis.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 6 is a screen shot of a second example screen of the therapist control system.

FIGS. 7A and 7B are partial screen shots of a third example screen of the therapist control system.

Figure 15D:
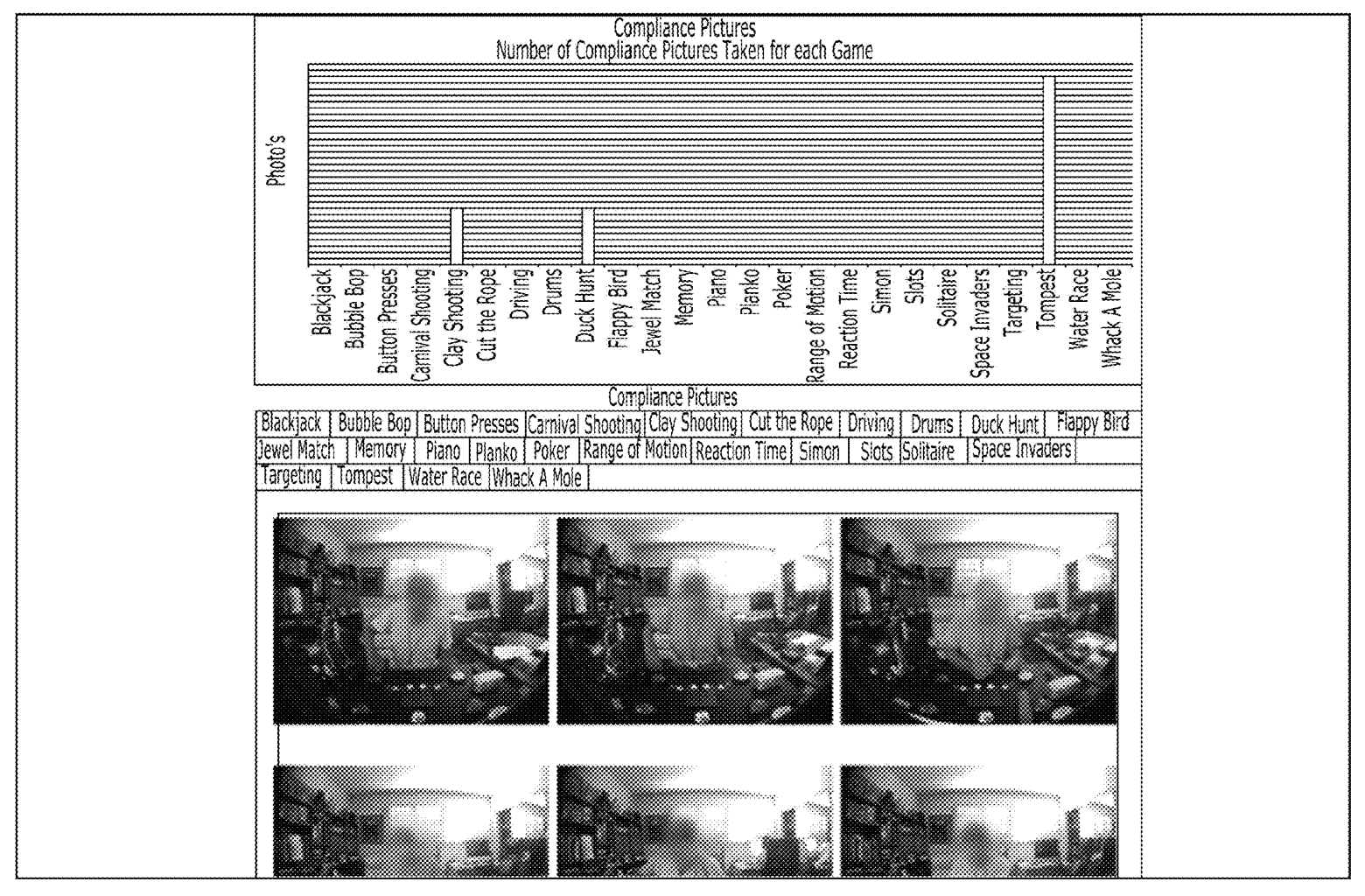

FIGS. 15A-15E are partial screen shots of a fourth example screen of the therapist control system.

DETAILED DESCRIPTION

As described above, it would be desirable to have a means with which rehabilitation therapy can be made more accessible to patients at a lower cost and that better motivates the patients to perform exercises at home. Disclosed herein are systems and methods for facilitating rehabilitation therapy that satisfy these goals. In some embodiments, a system includes a patient workstation that includes a table, computer, monitor, network connection device, and multiple user interface devices, all of which can be delivered to the patient's home as a complete package. Once the workstation is delivered, the patient can use the user interface devices to participate in various computer-based activities hosted by the computer, such as exercises and computer games that inherently require exercise, that have been specifically selected by a clinician, such as a physical therapist occupational therapist, physiatrist, nurse, or other medical professional, to exercise the parts of the patient's body that are in need of rehabilitation. The computer-based activities are structured as games that provide motivation to the patient to exercise at home that goes well beyond the regular motivation to physically improve.

In some embodiments, the system further includes a therapist control system that comprises software that can be used by the therapist to tailor a rehabilitation regimen specific to each individual patient. The therapist control system further includes software that can be used to track and analyze data collected by the patient workstation so that the therapist can evaluate the patient's performance of the home exercises and, if necessary, alter the patient's rehabilitation regimen. In some embodiments, the physical therapist can further visually and audibly interact with the patient by using the patient workstation as an interface with the patient while the patient performs the activities. This way, the therapist can provide online synchronous personal assistance to the patient in his or her home even through the therapist is in a different location.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
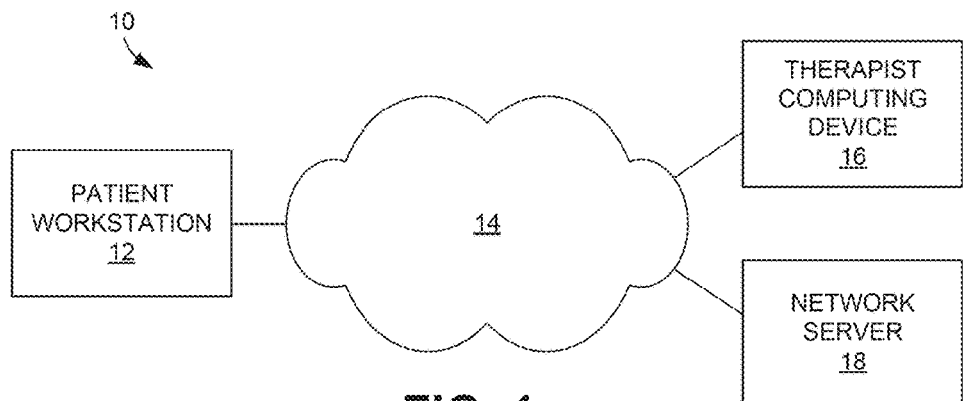
FIG. 1 is a block diagram of an embodiment of a system for facilitating rehabilitation therapy.
Figure 2:
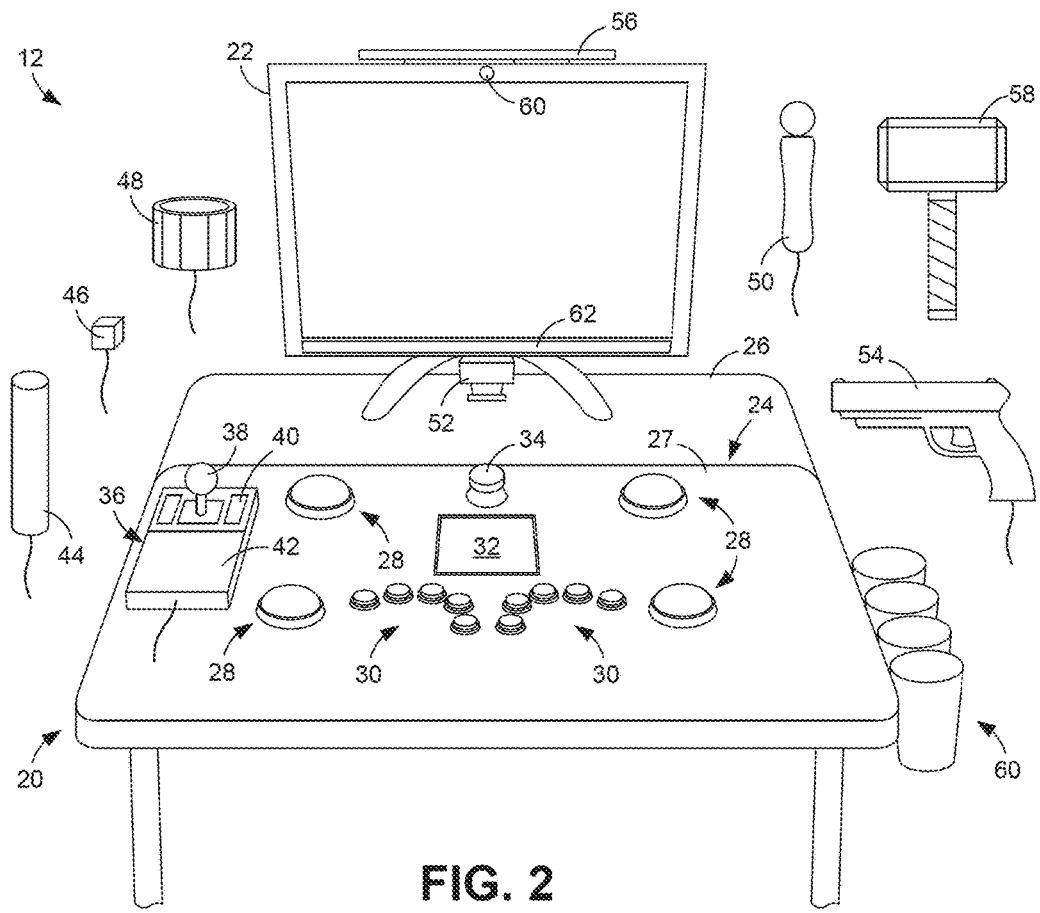
FIG. 2 is a schematic view of an embodiment of a patient workstation that can be used in the system of FIG. 1.

FIG. 1 illustrates an example embodiment of a system 10 for facilitating rehabilitation therapy, or rehabilitation system consistent with the above description. As shown in this figure, the system 10 generally comprises a patient workstation 12 that can connect to a network 14, such as the internet. An example embodiment for the patient workstation 12 is illustrated in FIG. 2 and described below. Also included in the system 10 shown in FIG. 1 are a therapist computing device 16 and a network server 18, which also can connect to the network 14. The therapist computing device 16 can comprise substantially any device that can be used to access and interact with the network server 18.

Accordingly, the computing device 16 can, for example, comprise a desktop computer, a laptop computer, a tablet computer, a smart phone, or the like. As described in greater detail in relation to FIG. 4, the network server 18 (a remote computer) can store and execute a therapist control system that includes various software that can be used by one or more therapists to design rehabilitation therapy regimens as well as monitor and evaluate the progress of patients performing their computer-based activities.

FIG. 2 illustrates an example embodiment for the patient workstation 12. In some embodiments, the patient workstation 12 comprises a portable, integrated system that comprises all of the components that a patient needs to perform at-home therapy prescribed by the patient's physical therapist. This is particularly beneficial in cases in which the patient lacks certain facilities, such as a computer and/or internet access, which may be needed to perform the activities in accordance with the design of the system 10, and further provides for standardization that ensures an appropriate environment for performance of the activities. As shown in FIG. 2, the patient workstation 12 can include a table 20. In some embodiments, the table 20 can be a folding table that can be easily transported and set up in the patient's home. The table 20 supports a computer 22 having an integrated monitor with which the patient can interact. While a computer 22 having an integrated monitor is shown in FIG. 2, it will be appreciated that the same functionality can be achieved with a computer and an independent monitor. As is described below, the computer 22 stores various software that can be executed to enable the patient to participate in computer-based activities, including computer games.

With further reference to FIG. 2, the table 20 also supports a tabletop console 24 that, in some embodiments, can be securely attached to the top surface 26 of the table such that it is integrated into the table. In some embodiments, the console 24 comprise a thin mat 27 that lies flat on the table surface 26 and that includes multiple integral user interface devices with which the user can enter inputs into the computer 22. In the embodiment of FIG. 2, the user interface devices include multiple (e.g., 4) distantly spaced large buttons 28, multiple (e.g., 10) closely spaced small buttons 30, a mouse pad 32, and a rotatable dial 34. Each of these devices is physically mounted to the mat 27 and cannot be removed from the mat without console disassembly. In addition, each of these devices is connected to the computer 22 with one or more cables (not visible in FIG. 2).

In some embodiments, the large buttons 28 are positioned on the tabletop console 24 so as to define four corners of a rectangular space on the surface of the mat 27. This space can, for example, be approximately 1 to 3 feet wide and approximately 1 to 2 foot deep from the perspective of a patient seated at the table 20. In some embodiments, the large buttons 28 can be illuminated (e.g., with different colors), either when commanded to do so by the computer 22 or when pressed or hit by the patient, depending upon the activity in which the patient is participating.

The small buttons 30 can be arranged in two generally lateral rows that are generally contained within the rectangular space defined by the large buttons 28. As shown in FIG. 2, the rows can be curved so as to be ergonomically adapted to receive the patient's fingertips. In such a case, the small buttons 30 can be pressed by individual fingers in similar manner to keyboard keys. The mouse pad 32 can also be positioned within the rectangular space, for instance, in the center of the space distal (from the perspective of the patient) of the small buttons 30. The dial 34 can also be positioned within the rectangular space distal of the mouse pad 32.

As can be appreciated from FIG. 2, the patient workstation 12 includes several auxiliary user interface devices that are not mounted to the mat 27 and, therefore, not integrated into the console 24. These devices can include a simple joystick device 36 having a joystick 38 and one or more input buttons 40. In the illustrated embodiment, the joystick device 36 further includes a wrist platform 42 proximal of the joystick 38 upon which the patient can rest his or her wrist when using the device. As the joystick device 36 is not mounted to the console 24, it can be moved by the patient to whatever position is most convenient for him or her.

Other user interface devices illustrated in FIG. 2 include a cylindrical member 44 that includes one or more force sensors, such as force transducers, that can measure the force with which the patient squeezes the member with his or her hand. In addition, the user interface devices include a cube member 46 that also includes one or more force sensors, such as force transducers, that can measure the force with which the patient pinches the member with his or her fingers. Further illustrated is a gesture control band 48 that can be worn on a limb, hand, or foot and that incorporates one or more angular accelerometers. A commercial example of such a band 48 is the Myo Gesture Control Band™ produced by Thalmic Labs.

The user interface devices of the patient workstation 12 can further include a wand controller 50 that can be tracked by a suitable motion tracking system that incorporates a camera, such as the camera 52 shown positioned on the table 20 in front of the computer/monitor 22. Commercial examples of such a controller and camera are the PlayStation Move Motion Controller™ and the PlayStation Eye™ camera. The workstation 12 can also comprise a gun controller 54 that includes a trigger that, when pulled, emits a beam of light whose trajectory can be detected by a suitable motion tracking system that incorporates a camera. In some embodiments, this motion tracking system can be same motion tracking system used to track the wand controller 50. In other embodiments, the motion tracking system can be a further motion tracking system that includes a further camera, such as the camera or motion tracking sensor 56 mounted to the top of the computer/monitor 22. A commercial example of a further motion tracking system is the Nintendo Wii™. Notably, in addition to tracking "shots" from the gun controller 54, the Wii™ tracking system can be positioned in different locations and configured to track movement of the patient's head, torso, and limbs.

Each of the above-described user interface devices is placed in communication with the computer 22. In some embodiments, each device directly connects to the computer 22 with a cable (i.e., a wired connection) so as to avoid the need to wirelessly connect the devices to the computer. In such cases, operation of the patient workstation 12 is simplified and easier to use by those who are not computer savvy. Of course, the same functionality can be achieved if one or more of the user interface devices are wireless. One user interface device shown in FIG. 2 that is neither connected to the computer 22 with a wire or wirelessly is a soft (e.g., foam) mallet 58, which can be used in conjunction with other user interface devices, such as the large buttons 28.

While several particular user interface devices have been illustrated in FIG. 2 and described above, it is noted that the patient workstation 12 need not include all of them. Furthermore, the workstation 12 can include other user interface devices not shown in FIG. 2. Accordingly, the embodiment of FIG. 2 is merely used as an example of the types of components the workstation 12 can comprise. Irrespective of the user interface devices that are included, the workstation 12 can further comprise one or more receptacles 60 attached to the table 20 that may be used to store devices when they are not in use.

Notably, the patient workstation 12 can comprise other features that facilitate the patient's home therapy. For example, the computer/monitor 22 can include a camera 60 and speakers 62 that facilitate video conferencing between the patient and the physical therapist. Such video conferencing can be performed while the patient is performing the computer-based activities. Although the camera 60 and speakers 62 are shown as being integrated into the computer/monitor 22, it will be appreciated that similar functionality can be achieved with a separate camera and/or separate speakers. In addition, the patient workstation 12 can further include a chair (not shown), such as a folding chair, that can be easily transported and that is of a size and configuration that works well with the table 20.

It is further noted that, while a particular configuration for the patient workstation 12 is illustrated in FIG. 1, other configurations can be used. For example, in other embodiments, the workstation 12 or part thereof can be contained in a briefcase or other highly portable object that can house workstation components such as the computer, monitor, and console. In such a case, the workstation can be mailed to the patient, opened, plugged in, and used on a tabletop.

Figure 3:
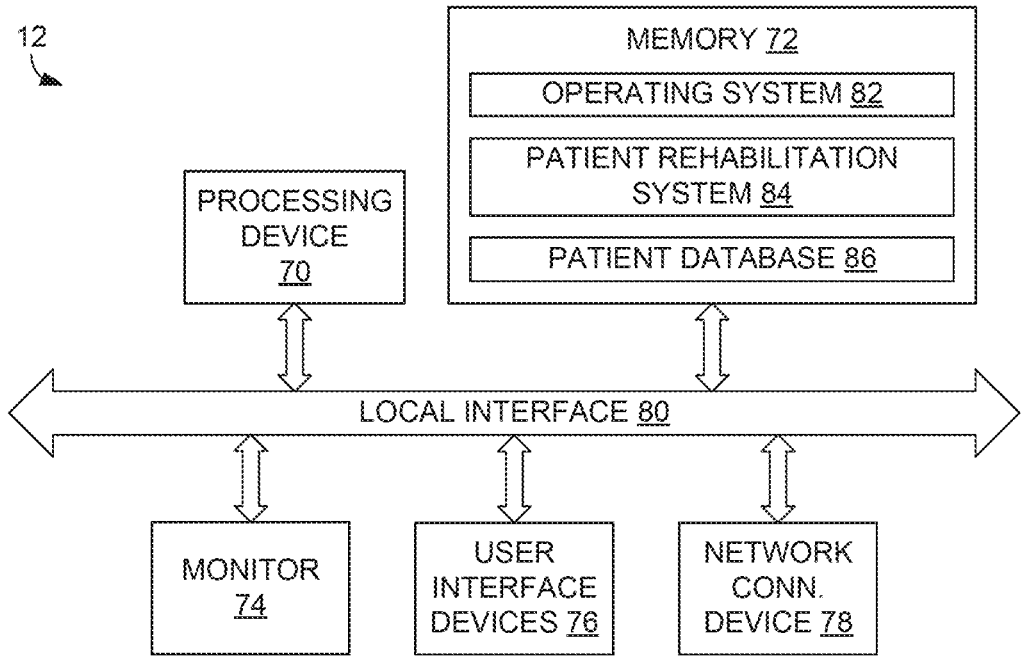
FIG. 3 is a block diagram of an embodiment of an architecture of a computer of the patient workstation of FIG. 2.

FIG. 3 illustrates an example computer architecture for the patient workstation 12. As shown in this figure, this architecture includes a processing device 70 and memory 72, which comprise part of the computer 22, a monitor 74, the user interface devices 76, which were described in relation to FIG. 2, and a network connection device 78, each of which is connected to a local interface 80. In some embodiments, the network connection device 78 comprises an internet modem.

The memory 72 (a non-transitory computer-readable medium) stores an operating system 82 and a patient rehabilitation system 84. The patient rehabilitation system 84 comprises one or more software programs (logic and/or executable instructions) that facilitate the aforementioned computer-based activities. In some embodiments, the system 84 comprises many different interactive games that, when played, provide rehabilitative exercise to the patient.

In addition, the patient rehabilitation system 84 comprises one or more software programs that collect and store (e.g., in a local patient database 86) data about the patient's use of the patient workstation 12. This data can comprise any information that may be useful to the patient or the physical therapist in evaluating the patient's progress. Examples of such information may include things like the times at which the patient uses the workstation, the durations of time the patient uses the workstation, the manner in which the patient uses the workstation, the activities in which the patient participates using the workstation, what user interface devices the patient uses while performing the activities, parameters that gauge the patient's skill in performing the activities, the difficulty levels of the activities in which the patient participates, and when and how long video conferences occur. Of course, other information can be collected and stored, if desired.

The patient rehabilitation system 84 further comprises one or more software programs that transmit the collected data to a device at which the patient's physical therapist can access it. In some embodiments, this comprises the network server 18. In such a case, the data can be transmitted with the network interface device 26 over the network 14 to the server 18 (FIG. 1). The data can be transmitted in a variety of ways. In some embodiments, the data can be transferred in real time as it is collected. In other embodiments, the data can be collected and stored locally in the local patient database 86 and intermittently transferred, for example, at one or more particular times of day.

Figure 4:
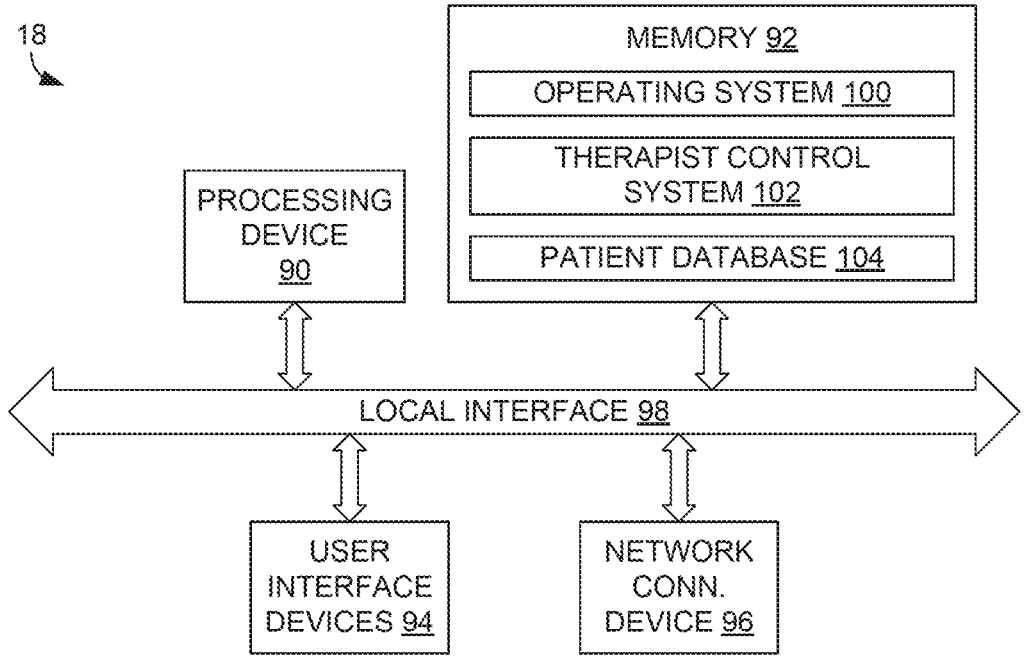
FIG. 4 is a block diagram of an embodiment of an architecture of a server of the system of FIG. 1.

FIG. 4 illustrates an example computer architecture for the network server 18. As shown in this figure, this architecture is similar to that shown in FIG. 3. Accordingly, it includes a processing device 90, memory 92, user interface devices 94, and a network connection device 96, each of which is connected to a local interface 98.

The memory 92 (a non-transitory computer-readable medium) stores an operating system 82 and a therapist control system 102. The therapist control system 84 comprises one or more software programs (logic and/or executable instructions) that enable therapists who access the network server 18 to custom tailor rehabilitation regimens for patients. As described in greater detail below, the therapists can design the regimens to include particular exercises, games, and user interface devices so that the patient can, according to the regimen, perform specific actions that are explicitly selected to rehabilitate one or more parts of the body. In some embodiments, the system 84 includes one or more algorithms that assist the therapist in selecting the exercises, games, and user interface devices for the patient based upon the results of a physical examination of the patient.

The therapist control system 84 further comprises one or more software programs that are configured to analyze the data collected by the patient workstations and provide qualitative and/or quantitative information that can be used to assess the patient's condition and progress with his or her rehabilitation therapy.

Also comprised by the memory 92 is a patient database 104 in which the data and analysis for multiple patients can be stored on a patient-by-patient basis. In some embodiments, this data and analysis can be shared with patient management software so that the data and analysis can be added to each individual patient's electronic medical file.

Figure 5:
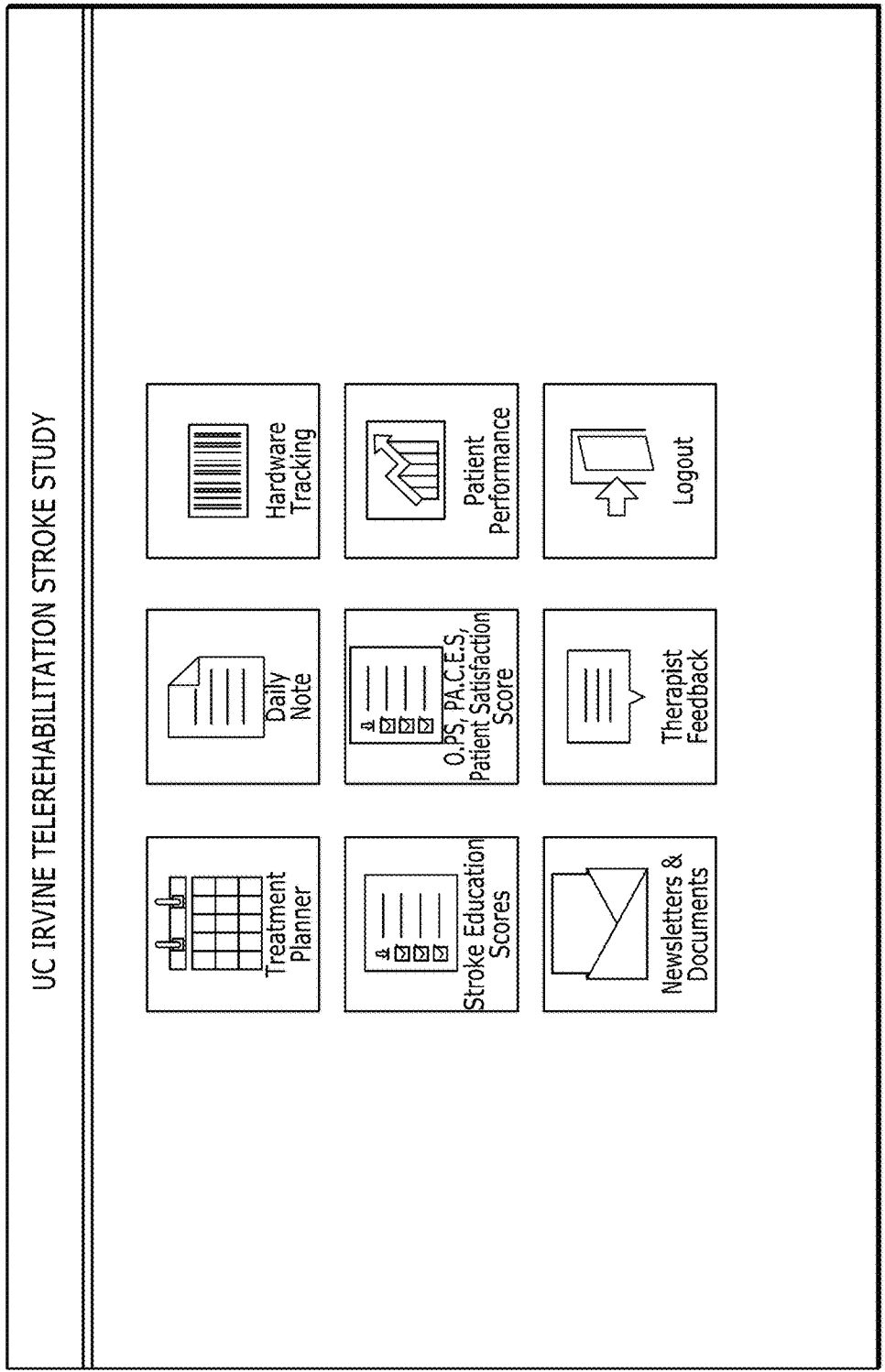
FIG. 5 is a screen shot of a first example screen of a therapist control system.

Having described example embodiments of a system above, examples of operation of the system will now be discussed. As mentioned above, a physical therapist can access the software of the therapist control system to design a rehabilitation regimen for a patient and track the patient's progress. FIG. 5 illustrates an example screen of the control system that the therapist can access. As can be appreciated from this figure, the screen can present various options to the therapist, including a "Treatment Planner" functionality and a "Patent Performance" functionality. Regarding treatment planning, the therapist can plan the patient's treatment based upon the patient's condition. To assess this condition, therapist can conduct an in-person physical examination of the patient, which may be conducted in the therapist's office, the patient's home, or another location. In cases in which the patient is an individual with stroke, the therapist can perform a Fugl-Meyer assessment with which various patient movements are rated from 0 to 2, 0 indicating the patient cannot perform the movement, 1 indicating that the patient can partially perform the movement, and 2 indicating that the patient can fully perform the movement. If the patient has a different disease as the basis for rehabilitation therapy, then an appropriate corresponding assessment can be scored in this manner. In some embodiments, the therapist control system comprises one or more algorithms that are designed to receive these scores as inputs and automatically provide therapy recommendations to the therapist based upon the scores. In such a case, the therapist can enter the various scores into a suitable screen of the therapist control system, such as the screen shown in FIG. 6.

Figure 7B:
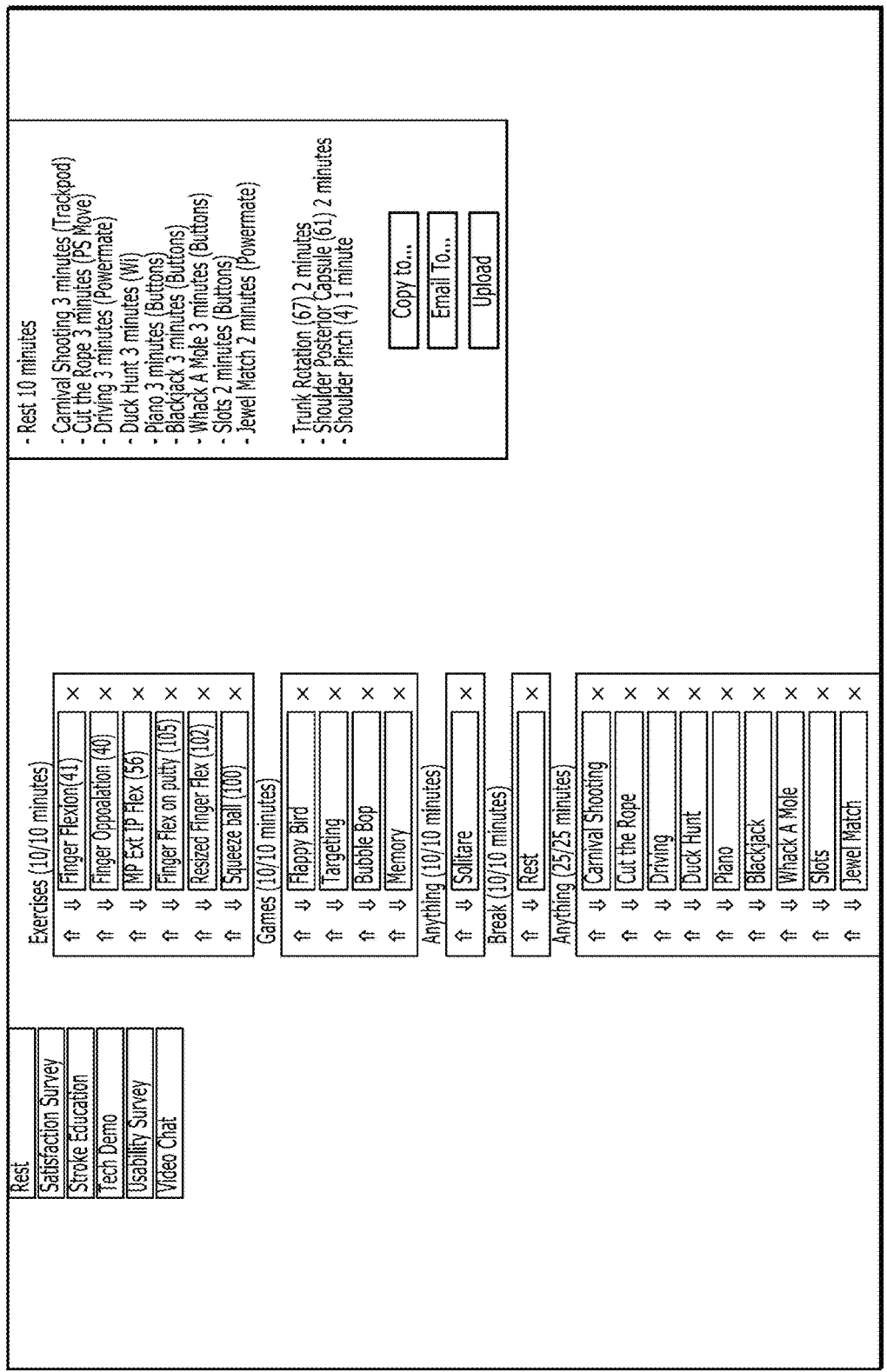

Once the scores have been entered, one or more screens can be presented to the therapist with the therapy recommendations. FIGS. 7A and 7B illustrate an example of such a screen. As shown in these figures, the therapist control system presents potential activities for the patient based upon the particular needs of the patient (e.g., decreased grip strength). These activities include exercises and games that, when performed by the patient, provide exercise to the area or areas in need of rehabilitation. In some embodiments, the therapist can either accept the recommendations presented by the therapist control system or ignore them and select his or her own activities for the patient. In other embodiments, some activities can be mandatory while others may be selected by the therapist. Regardless, the activities that are recommended and/or selected by the therapist can be added to one or more rehabilitation itineraries for the patient that will form part of the patient's rehabilitation regimen.

After the rehabilitation itineraries have been created, the patient workstation computer can be programmed to facilitate patient activities in accordance with the itineraries. In addition to programming the particular activities that are to be performed, other aspects of the therapy can be programmed into the computer before it is provided to the patient. For example, the computer can be programmed to specify when the activities are to be performed, how long the activities are to be performed, the number and duration of breaks during activities, the user interface devices to be used during the activities, how the user interface devices are to be used during the activities, the difficulty level to be used for each activity, and any other parameters that may be relevant to providing high-quality rehabilitation therapy to the patient.

Once the patient workstation computer has been programmed, the workstation can be provided to the patient for home use. In some embodiments, the entire workstation, including all of its components, can be delivered to the patient's home and set up within the home by the physical therapist of a representative thereof. This facilitates a "drop, plug, and play" functionality in which the workstation can be dropped off at the patient's home and plugged in so as to enable the patient to use ("play" with) the workstation without having to perform any setting up or installation on his or her own.

Figure 8:
FIG. 8 is a screen shot of a first example screen of a patient rehabilitation system.
Figure 9:
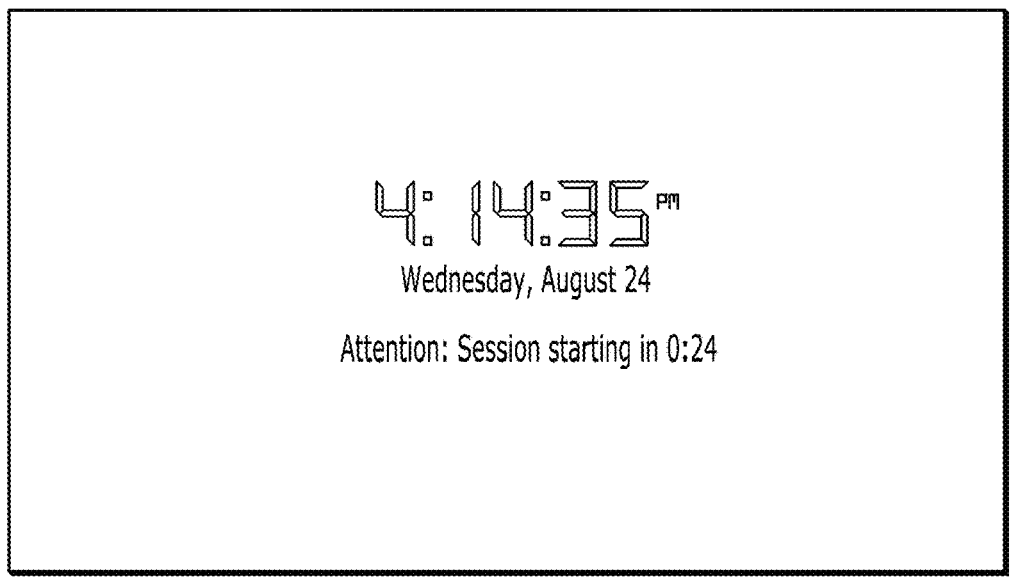
FIG. 9 is a screen shot of a second example screen of the patient rehabilitation system.

The patient interface is also designed so as to be simple to use. To that end, the workstation can be configured to turn on when any input is received from any of its user interface devices. In some embodiments, a virtual physical therapist screen can appear on the monitor to assist the patient in using the workstation. FIG. 8 shows an example of such a screen. As indicated in this screen, the patient can continue on from the screen by pressing a "Go" button, which can be any button of the workstation labeled as such (e.g., a joystick button). In some embodiments, the workstation can also be configured to remind the patient as to an upcoming therapy session. FIG. 9 illustrates an example screen that does this. As shown in the FIG. 9, the screen can identify the current time and provide a countdown to a scheduled therapy session.

Figure 10:
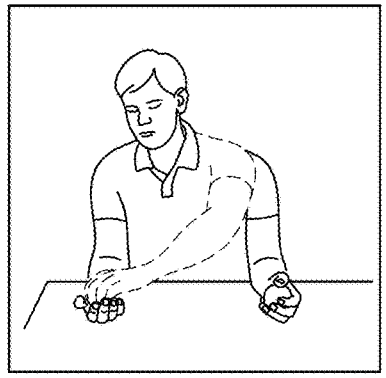
FIG. 10 is a screen shot of a third example screen of the patient rehabilitation system.

As described above, the activities that are to be performed by the patient can include exercises as well as games, which inherently provide exercise. The patient workstation can not only be used to play the games but also provide instruction as to how to perform the exercises. FIG. 10 shows an example screen that describes and illustrates one such exercise. In addition to providing instruction as to how the exercise is performed, the screen can further act as a timer for the duration with which the exercise is performed.

One of the greatest benefits of the patient workstation are the games that can be played with the workstation given that such games provide very strong intrinsic motivation to patients to perform the exercises integral to their therapy. Such games remove much of the tedium normally associated with home-based physical/occupational therapy and with home-based exercises and studies conducted by the inventors have revealed that much greater compliance with home exercise is achieved using the games. As described above, the workstation computer can store the games, which can be played using a variety of user interface devices such that the specific movements most likely to provide improvement in the patient's condition can be performed.

Numerous games can be included with the patient workstation 12 and used to satisfy various therapy treatment objectives. In some embodiments, the therapy treatment objectives can include:
1. Proximal Strength. Scapular or scapulohumeral, shoulder flexion/extension, shoulder abduction/adduction, shoulder internal/external rotation, or elbow flexion/extension strength in all planes of movement.
2. Proximal Motor Control. Coordination/motor control of the upper extremity at the shoulder, elbow or both.
3. Distal Strength. Forearm pronation/supination, wrist flexion/extension, wrist radial/ulnar deviation or gross finger flexion/extension strength.
4. Distal Motor Control. Coordination/motor control of the upper extremity at the forearm, wrist, or hand.
5. Grip Strength. Finger flexion strength for gripping.
6. Pinch Strength. Index finger and thumb opposition strength.
7. Fine Motor Control. Coordination of the fingers.

Examples of games, user interface devices that can be used in the games, and therapy treatment objectives that can be satisfied by playing the games with the user interface devices include:
1. Black Jack
   (a) Goal: Beat the blackjack with card hands totaling 21 or less.
   (b) Devices/Objectives:
       Small Buttons: Proximal Motor Control, Distal Strength, Distal Motor Control
2. Bubble Pop
   (a) Goal: Pop as many bubbles as possible before they reach the top.
   (b) Devices/Objectives:
       Wand Controller: Proximal Strength, Proximal Motor Control
       Gun Controller: Proximal Strength, Proximal Motor Control
       Mouse Pad: Distal Motor Control, Fine Motor Control
3. Button Presses
   (a) Goal: Press the button that appears on the screen.
   (b) Devices/Objectives:
       Small Buttons: Proximal Motor Control, Distal Strength, Distal Motor Control
4. Carnival Shooting
   (a) Goal: Shoot the yellow and white ducks (not red ones) before they disappear.
   (b) Devices/Objectives:
       Wand Controller: Proximal Strength, Proximal Motor Control Gun Controller: Proximal Strength, Proximal Motor Control
Mouse Pad: Distal Motor Control, Fine Motor Control
5. Clay Shooting
    (a) Goal: Shoot the clay target down before it disappears into the distance.
    (b) Devices/Objectives:
        Wand Controller: Proximal Strength, Proximal Motor Control
        Gun Controller: Proximal Strength, Proximal Motor Control
        Mouse Pad: Distal Motor Control, Fine Motor Control
6. Cut the Rope
    (a) Goal: Cut the candy rope and feed the little green creature.
    (b) Devices/Objectives:
        Wand Controller: Proximal Strength, Proximal Motor Control
        Gun Controller: Proximal Strength, Proximal Motor Control
        Mouse Pad: Distal Motor Control, Fine Motor Control
7. Driving
    (a) Goal: Control the car to stay on the driving path between the colored cones.
    (b) Devices/Objectives:
        Dial: Distal Strength, Distal Motor Control, Fine Motor Control
        Gesture Control Band: Distal Strength, DMS
        Mouse Pad: Distal Motor Control, Fine Motor Control
8. Drums
    (a) Goal: Play drumming music by pushing buttons (each button has a different drum beat).
    (b) Devices/Objectives:
        Small Buttons: Proximal Motor Control, Distal Strength, Distal Motor Control
9. Duck Hunt
    (a) Goal: Shoot down the flying ducks.
    (b) Devices/Objectives:
        Wand Controller: Proximal Strength, Proximal Motor Control
        Gun Controller: Proximal Strength, Proximal Motor Control
        Mouse Pad: Distal Motor Control, Fine Motor Control
10. Flappy Bird
    (a) Goal: Fly the bird as far as you can through the openings in the pipes without hitting a pipe.
    (b) Devices/Objectives:
        Small Buttons: Proximal Motor Control, Distal Strength, Distal Motor Control
        Squeeze Cylinder: Grip Strength
        Pinch Cube: Distal Motor Control, Pinch Strength
        Wand Controller: Proximal Strength, Proximal Motor Control
        Mouse Pad: Distal Motor Control, Fine Motor Control
11. Jewel Match
    (a) Goal: Rotate the wheel to line up and catch the same colored jewel.
    (b) Devices/Objectives:
        Dial: Distal Strength, Distal Motor Control, Fine Motor Control
        Gesture Control Band: Distal Strength, DMS
        Mouse pad: Distal Motor Control, Fine Motor Control
12. Memory
    (a) Goal: Turn over pairs of matching cards.
    (b) Devices/Objectives:
        Wand Controller: Proximal Strength, Proximal Motor Control
        Gun Controller: Proximal Strength, Proximal Motor Control
        Mouse Pad: Distal Motor Control, Fine Motor Control
13. Piano
    (a) Goal: Play piano music by pushing buttons (each button plays a different piano key).
    (b) Devices/Objectives:
        Small Buttons: Proximal Motor Control, Distal Strength, Distal Motor Control
14. Plinko
    (a) Goal: Select and drop a ball onto an arrowed space at top of pegboard.
        The goal is to drop in a green space to gain points, whereas landing on a red space will lose you points.
    (b) Devices/Objectives:
        Wand Controller: Proximal Strength, Proximal Motor Control
        Gun Controller: Proximal Strength, Proximal Motor Control
        Mouse Pad: Distal Motor Control, Fine Motor Control
15. Poker
    (a) Goal: Play poker by dealing and holding cards using the buttons.
    (b) Devices/Objectives:
        Small Buttons: Proximal Motor Control, Distal Strength, Distal Motor Control
16. Range Of Motion
    (a) Goal: Move the gauge into the target area and hold it until the progress meter is completed.
    (b) Devices/Objectives:
        Wand Controller: Proximal Strength, Proximal Motor Control
        Gun Controller: Proximal Strength, Proximal Motor Control
        Mouse Pad: Distal Motor Control, Fine Motor Control
17. Reaction Time
    (a) Goal: Rest the hand on the indicated button until the screen turns red and then to press the target stimulus button as fast as you can when the screen turns green.
    (b) Devices/Objectives:
        Small Buttons: Proximal Motor Control, Distal Strength, Distal Motor Control
18. Simon
    (a) Goal: Push buttons in a sequence to reproduce the order of colored buttons (each with a particular tone) that were presented on the screen.
    (b) Devices/Objectives:
        Large Buttons: Proximal Motor Control, Distal Strength, Distal Motor Control
19. Slots
    (a) Goal: Push a button to start/stop spinning reel to line up matching fruits.
    (b) Devices/Objectives:
        Small Buttons: Proximal Motor Control, Distal Strength, Distal Motor Control
        Squeeze Cylinder: Grip Strength
        Pinch Cube: Distal Motor Control, Pinch Strength
20. Solitaire
    (a) Goal: Hover over cards and push buttons to pick-up/release cards, in order to build up four stacks of cards starting with an ace and ending with a King, all of the same suit.

Figure 11:
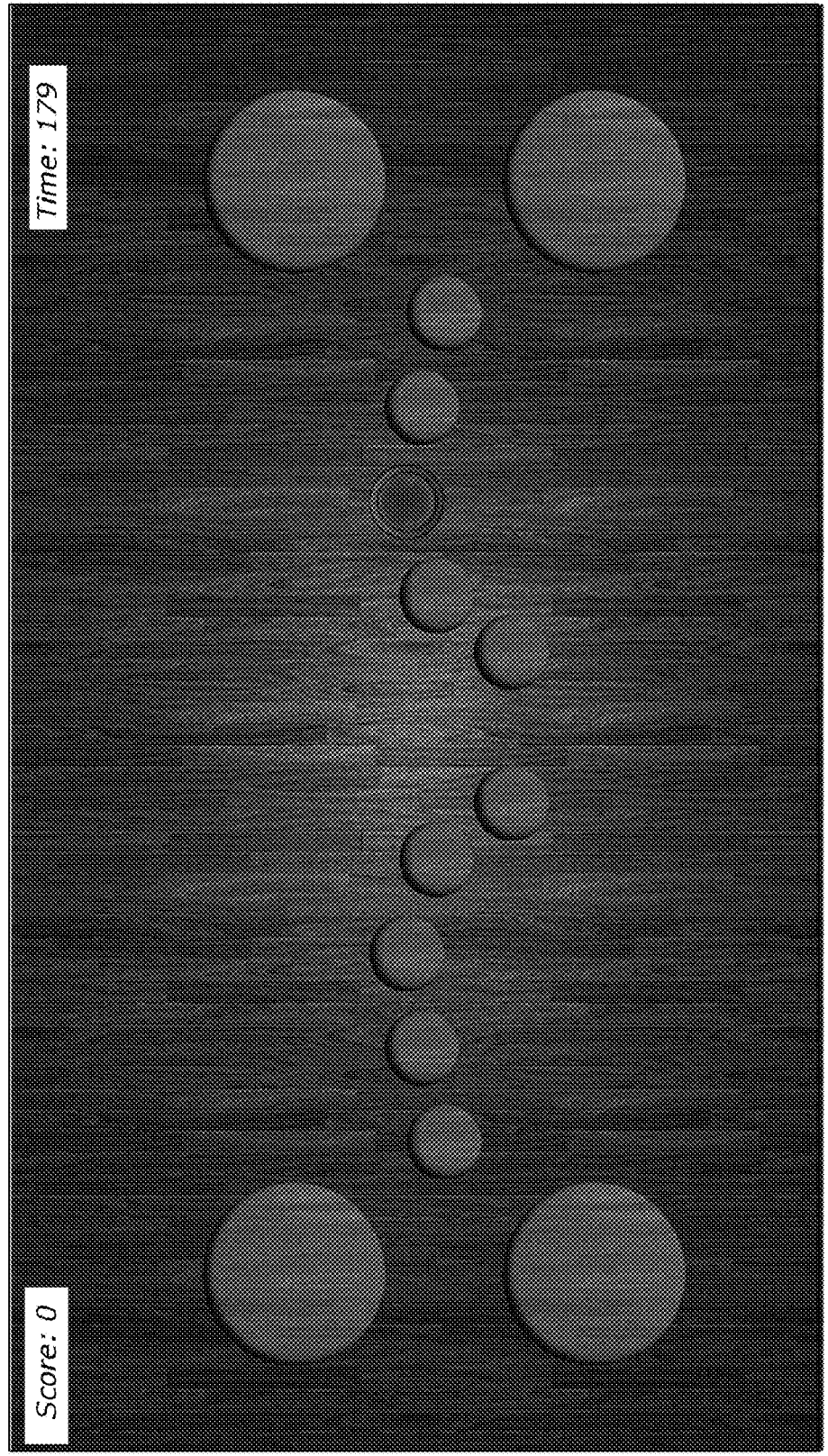
FIG. 11 is a screen shot of a fourth example screen of the patient rehabilitation system.
Figure 12:
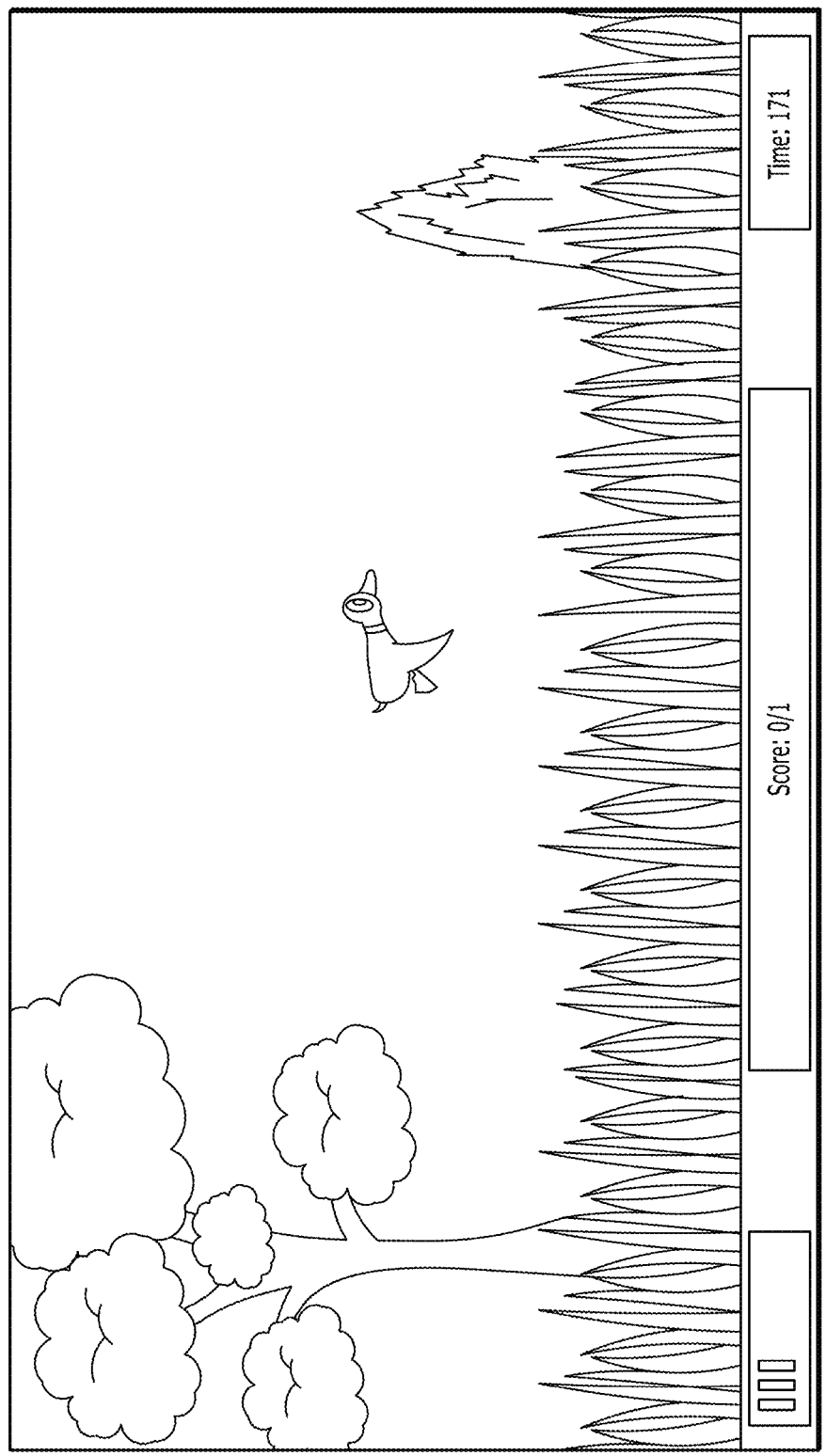
FIG. 12 is a screen shot of a fifth example screen of the patient rehabilitation system.

(b) Devices/Objectives:
Wand Controller: Proximal Strength, Proximal Motor Control
Gun Controller: Proximal Strength, Proximal Motor Control
Mouse Pad: Distal Motor Control, Fine Motor Control
21. Space Invaders
  (a) Goal: Fire at descending aliens by moving a cannon shooter horizontally across the bottom of the screen.
  (b) Devices/Objectives:
    Dial: Distal Strength, Distal Motor Control, Fine Motor Control
    Gesture Control Band: Distal Strength, DMS
    Mouse Pad: Distal Motor Control, Fine Motor Control
22. Targeting
  (a) Goal: Move the gauge into the red target zone and hold it there until the progress meter is complete.
  (b) Devices/Objectives:
    Squeeze Cylinder: Grip Strength
    Pinch Cube: Distal Motor Control, Pinch Strength
    Gesture Control Band: Distal Strength, DMS
    Dial: Distal Strength, Distal Motor Control, Fine Motor Control
    Wand Controller: Proximal Strength, Proximal Motor Control
23. Tempest
  (a) Goal: Move the shooter to the appropriate segment on the circle to shoot the aliens before they reach the middle of the circle.
  (b) Devices/Objectives:
    Dial: Distal Strength, Distal Motor Control, Fine Motor Control
    Gesture Control Band: Distal Strength, DMS
    Mouse Pad: Distal Motor Control, Fine Motor Control
24. Water Race
  (a) Goal: Shoot water at the colored target to move a colored horse across the finish line.
  (b) Devices/Objectives:
    Dial: Distal Strength, Distal Motor Control, Fine Motor Control
    Gesture Control Band: Distal Strength, DMS
    Mouse Pad: Distal Motor Control, Fine Motor Control
25. Whack-a-Mole
  (a) Goal: Hit the button with the mallet when it lights up.
  (b) Devices/Objectives:
    Large Buttons: Proximal Motor Control, Distal Strength, Distal Motor Control FIG. 11 shows an example screen shot from the button press game in which a specific small button on the tabletop console (e.g., a button 30 in FIG. 2) must be pressed by the patient when a virtual representation of that particular button is displayed in the screen. FIG. 12 shows an example screen shot of the duck hunt game in which the patient uses the gun controller (e.g., controller 54 in FIG. 2) to shoot ducks that fly across the screen.

Figure 13:
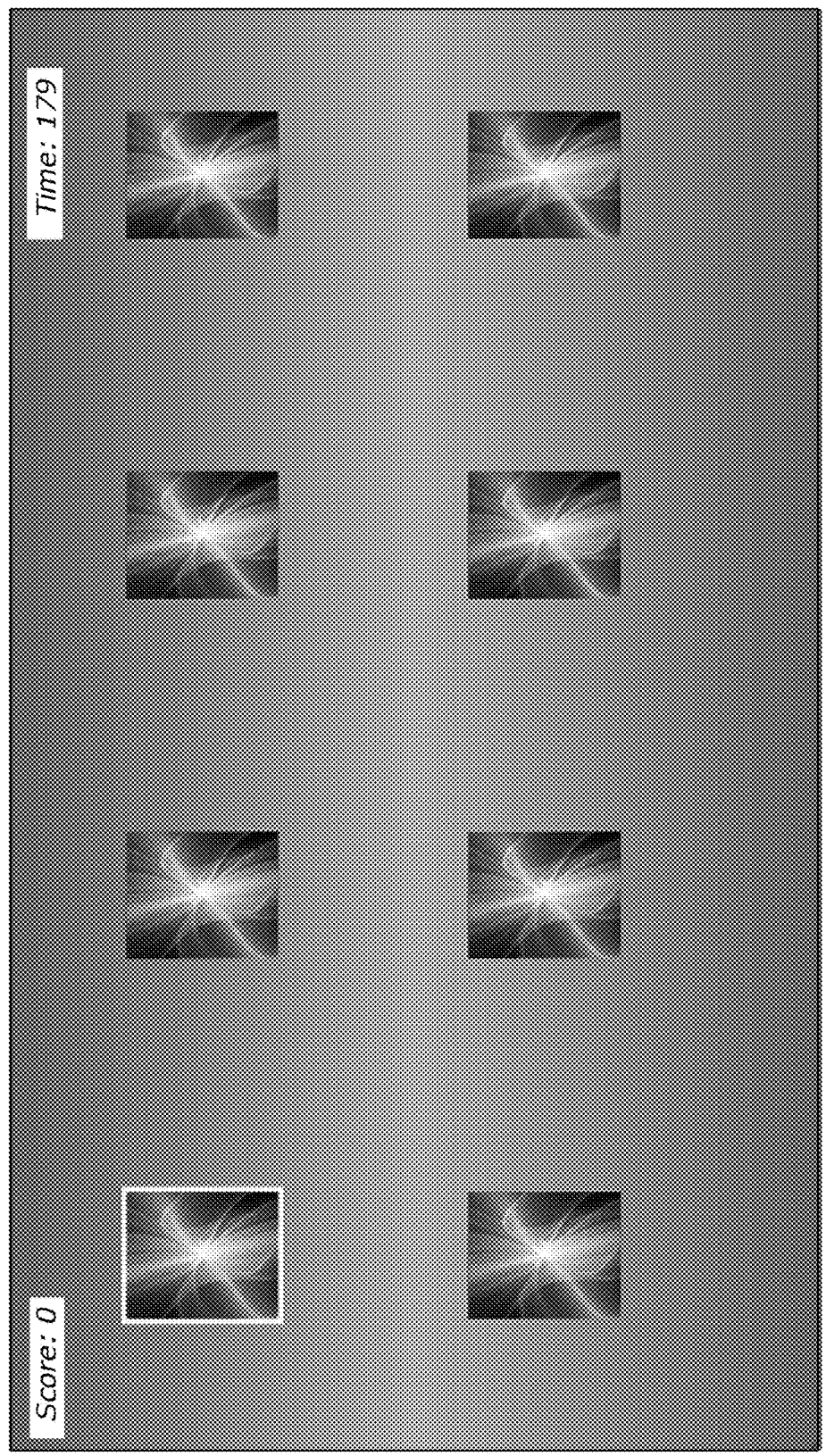
FIG. 13 is a screen shot of a sixth example screen of the patient rehabilitation system.
Figure 14:
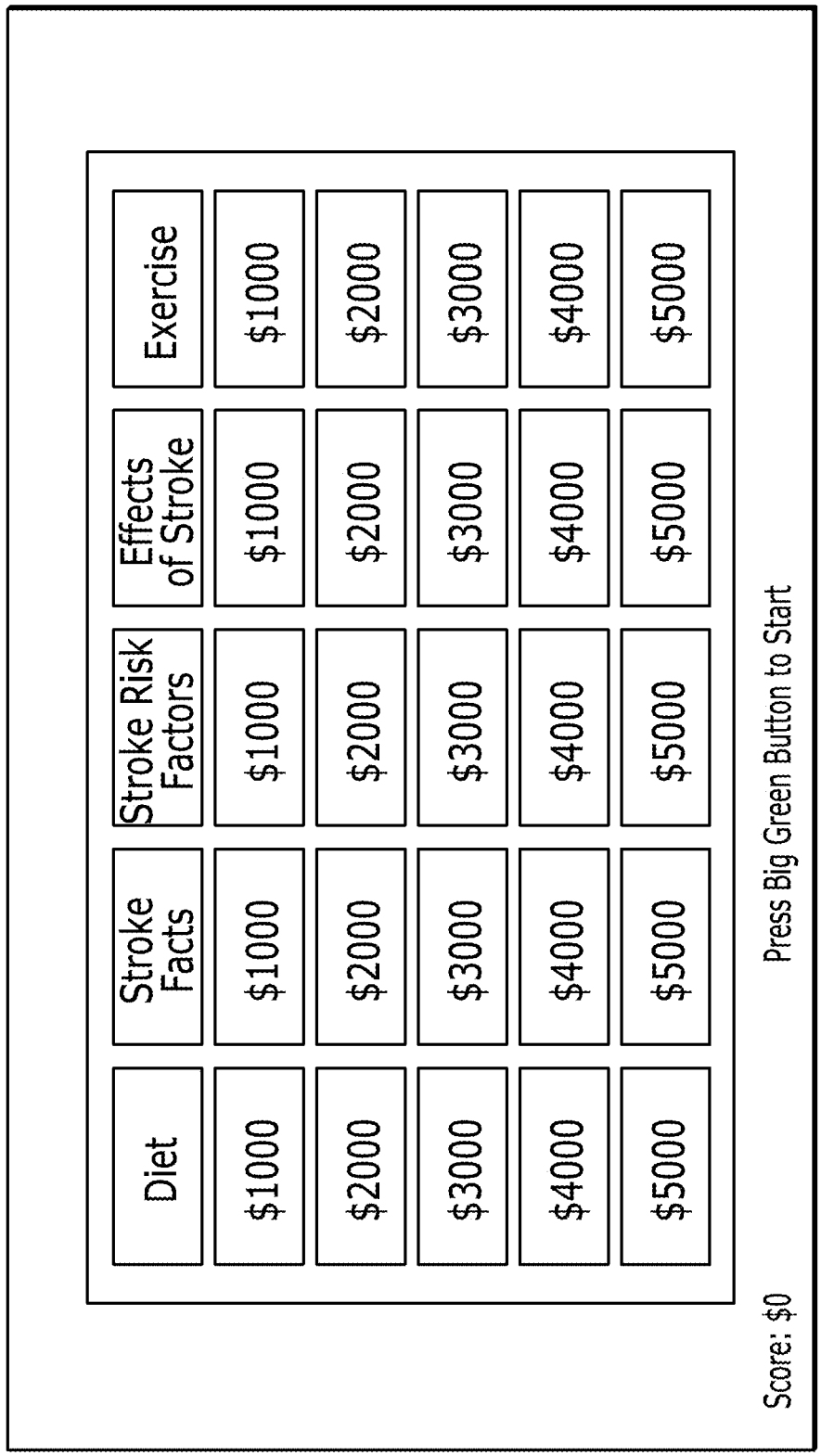
FIG. 14 is a screen shot of a seventh example screen of the patient rehabilitation system.
Figure 15A:
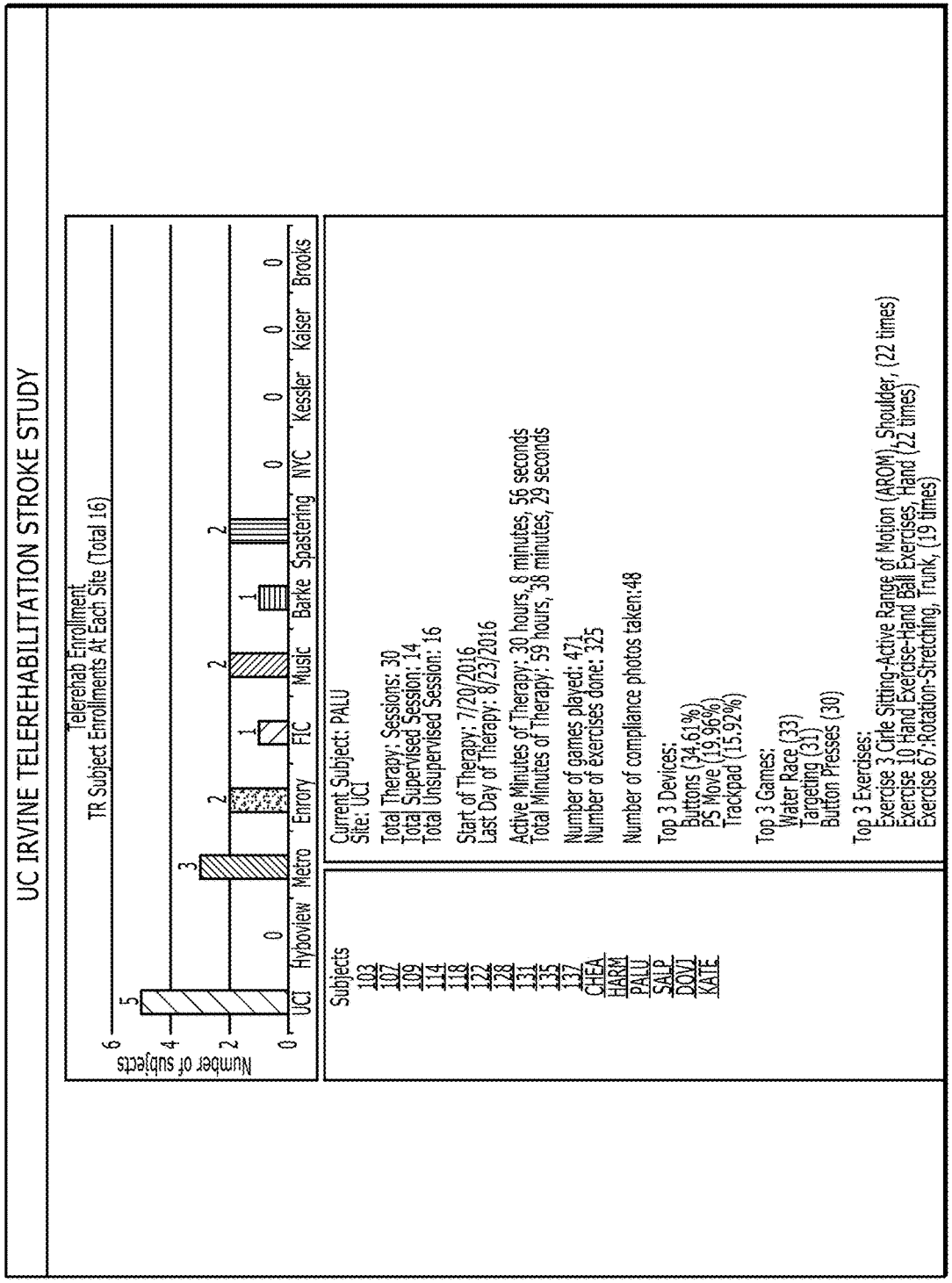
Figure 15B:
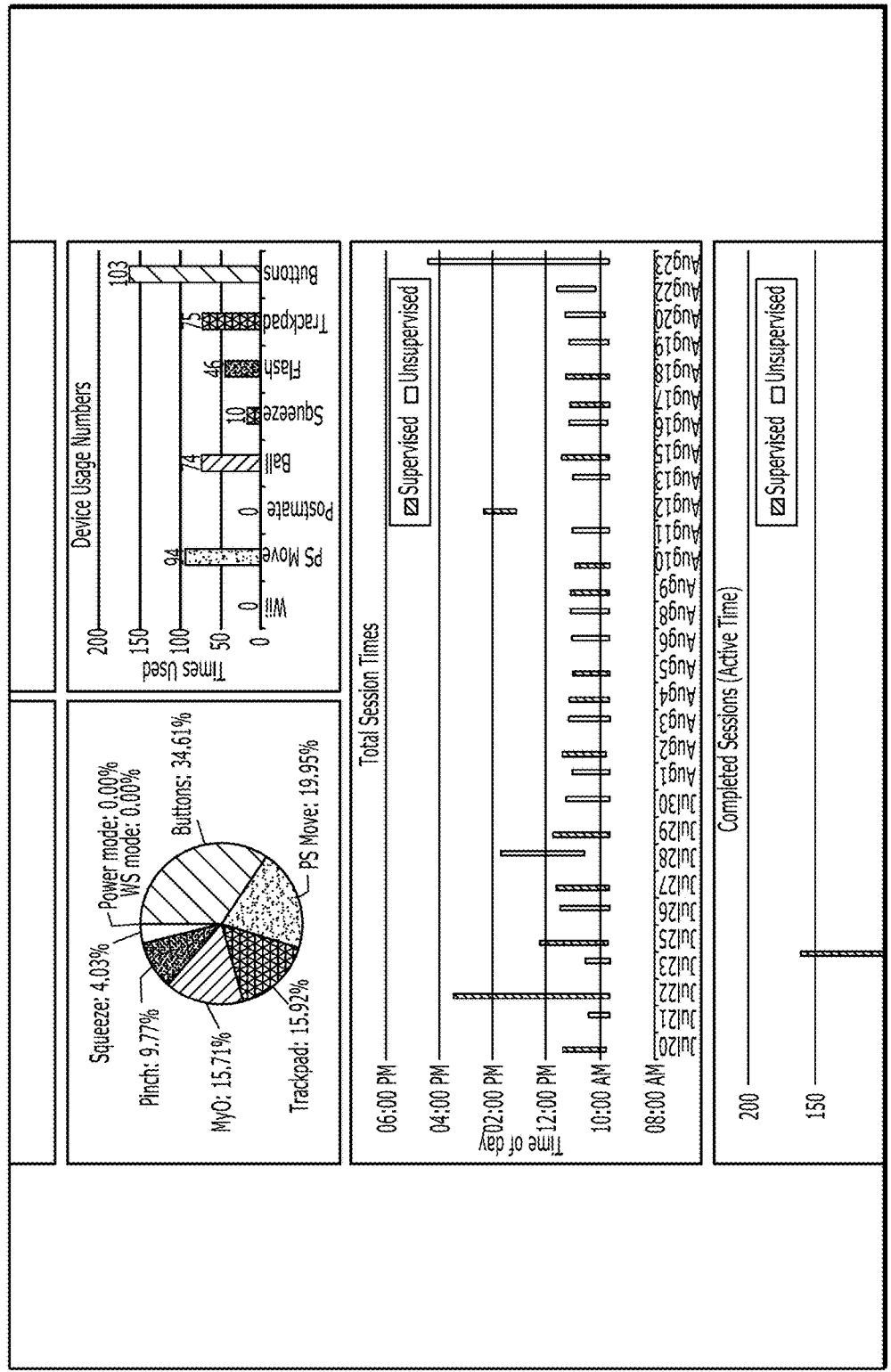
Figure 15C:
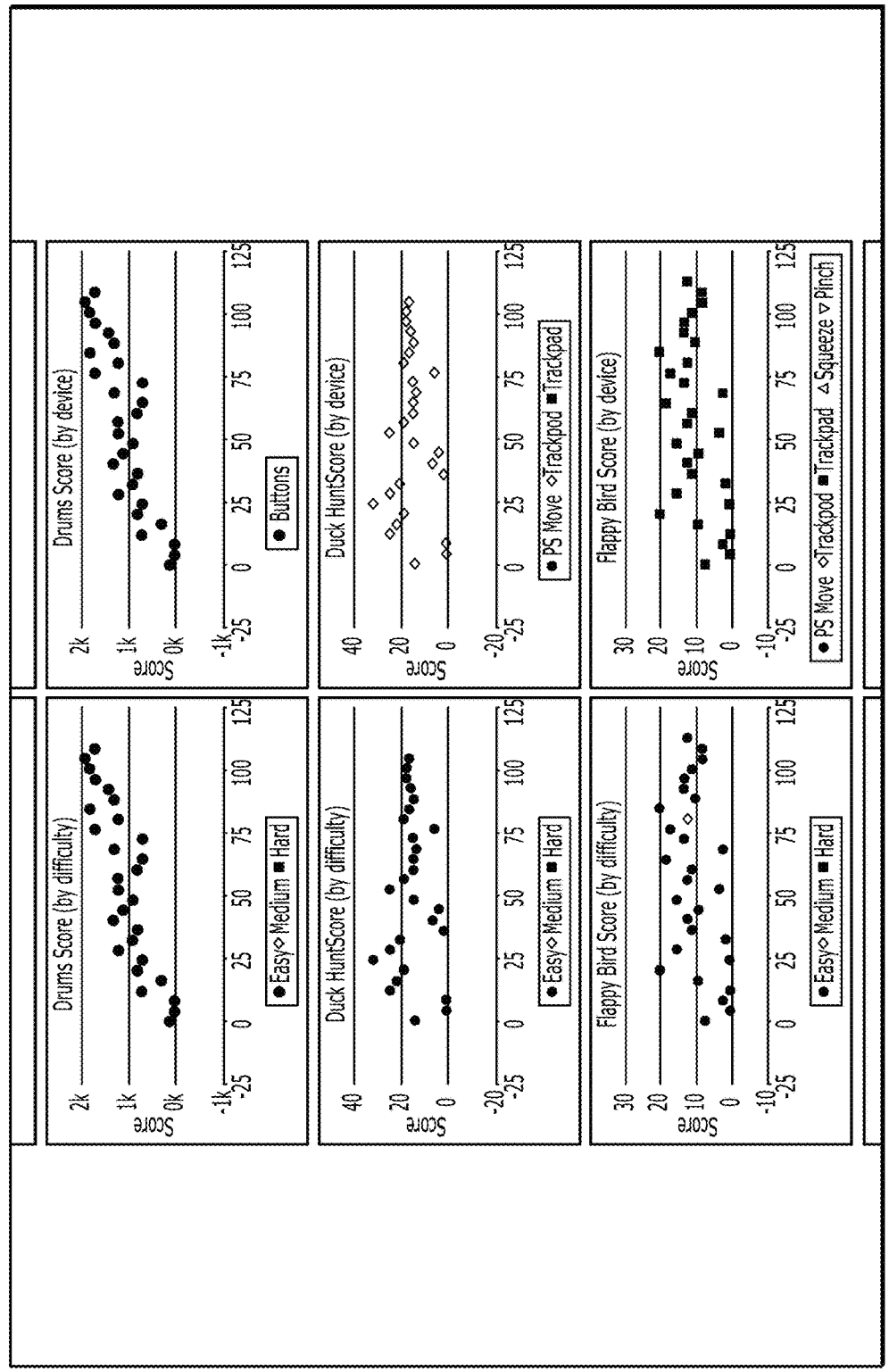

In addition to games that are focused on physical exercise, the workstation computer can also store and execute games that are focused on cognitive ability and/or knowledge. FIG. 13 shows an example screen shot of the memory game, a cognition game, in which the patient must remember the locations or cards displayed with the monitor. FIG. 14 shows an example of a knowledge game that can be used to educate the patient on a relevant topic, such as symptoms of a particular condition that the patient may have or risk factors for that condition. In this case, the game comprises a quiz show game in which the patient selects a particular category and dollar amount and is then asked a question associated with the category and dollar amount.

As described above, the physical therapist can access data concerning the activities performed by the patient while using the patient workstation for purposes of evaluation and, potentially, changing the patient's rehabilitation regimen. FIGS. 15A-15E illustrate an example screen that contains such data. A wide variety of information can be provided to the physical therapist. As is apparent from the figures, the information can include the total therapy sessions, the fractions of these sessions that were supervised or unsupervised, the start date of the therapy, the last day of the therapy, the exercises performed, the games played, the user interface devices used, patient compliance, patient game scores, images of the patient performing activities, etc. Generally speaking, any data that can be collected by the patient workstation can be presented to the physical therapist to assist him or her in facilitating the patient's recovery to the greatest extent possible.

The system described in the foregoing provides many advantages not provided by current rehabilitation therapy solutions. For one thing, the system provides a holistic approach to rehabilitation therapy: recovery of function and independence is related to patient knowledge, patient empowerment, and prevention of known potential complications. Moreover, the system can be used for patients having a variety of conditions as well as degrees of impairment.

The system is modular and open to reconfiguration and personalization. The same system can be used to treat patients with many different diagnoses and can be adjusted and personalized (by the therapist, patient, or both) to be useful to persons with any degree of disease severity. This also means that, as a patient improves, treatment through this system can be adjusted to remain useful.

The system can be used to provide rehabilitation therapy in many different settings that can be remote from the therapist. Because the system is portable and transportable, the same rehabilitation therapy can be provided in the home, clinic, or any other setting.

The treatment provided by the system can be remotely revised by persons providing rehabilitation care. The communication components of this system enable a remote therapist to input progress reports and other forms of patient data and to output a revised treatment plan that is uploaded silently and rapidly to the patient's workstation.

The system also opens the door to providing the same rehabilitation therapy to a given patient across different locations, e.g., from rehabilitation hospital to skilled nursing facility to one home to another home, anywhere in the world. Smoothing transitions in rehabilitation care is a major plus provided by the system, as problems during transitions of care account for a disproportionate extent of adverse events and readmissions, which are topics that attain great significance in the Affordable Care Act and Accountable Care Organizations era. Improvements in the continuity of care for patients moving through the stages of rehabilitation therapy can also improve short-term and long-term therapist-patient relations. This system is specifically designed to promote favorable forms of recovery by employing known principles of neural plasticity and motor learning including high intensity therapy that allows for hundreds of movement repetitions, keeping the patient continuously challenged at an individualized level, variability, high interest and motivation, and regular provision of feedback.

The system further provides the experience needed to maximize effects from neuromodulatory treatments. For many treatments that aim to modulate neural function after a brain injury, such as medications or brain stimulation, abundant data suggests that treatment effects require concomitant behavioral training or shaping. Recovery treatments require experience-dependent brain plasticity and the disclosed system is well suited to apportion, provide, and measure the rehabilitation experience.

The system also provides improved motivation to patients for them to practice their assigned rehabilitation activities. Motivation of patients is improved by the system in at least in four ways: (1) "gameifying" the exercises infuses intrinsic enjoyment of the activity; (2) flexible and continuous tailoring of exercise that are difficulty to master avoids excessive challenges and boredom; (3) the system's interactive components (especially the video conferencing) sidestep a common reason for patients to reject internet-based rehabilitation as a substitute for interaction with a real person; and (4) recording of practice and performance enables accountability to self, therapist, and third-party payers.

The system further provides a broad standardization of care. Some forms of rehabilitation therapy benefit from provision in a standardized manner. Whether using a single central care provider or multiple providers, the system facilitates this, for example, providing the same form of therapy to many patients who are scattered over time and space.

The system also provides a quantitative measurement of quality of patient performance. Patients and therapists are provided with several measures of patient performance, progress, and improvements/declines. This provides information regarding a patient's impairments and functional status, and reveals how these change over time. The use of multiple assessment instruments, methods, and devices provides a broad view of patient status and a more comprehensive profile than any single measurement approach.

The system further provides quantitative measurement of amount of patient performance in terms of information regarding how much therapy a patient is actually performing with the system. Such data can be valuable to a clinical trial where measurement of number of minutes of therapy each day is a critical variable or to an HMO that wishes to confirm patient compliance justifies a rehabilitation expense.

The system also provides patient accountability. In some settings, rehabilitation therapy is a valuable commodity. Therefore, in such settings, rehabilitation therapy might be most judiciously provided in relation to effective utilization. Having a patient be accountable can allow the provider of care, such as an HMO or an insurer, to measure how the patient is contributing to his/her own care, and apportion therapy based on this measure of accountability.

The system can further provide feedback that can come in many forms, be in real time, and be used to improve future performances. As an extension of this, real-time measures of patient performance can be used to adjust the difficulty level of rehabilitation games and exercises on the fly according to pre-selected rules.

The system enables the user to interface with many current rehabilitation devices. As noted above, the system includes many games, which can be used with a range of different user interface devices. Numerous devices can be adapted in this regard, including most or all commercially available rehabilitation devices.

The system also can generate regular progress reports, which can focus on patient goals, therapist goals, or feedback (to patient or therapist) of patient performance and usage statistics. Such reports can be in real time or retrospective, and can cover data over a minute, an hour, a day, or a year's efforts. In this way, the system introduces a means to generate objective, quantitative documentation of a patient's home rehabilitation efforts.

The system also enables internet-based communication. The communication components of the system allow live videoconference dialogues between patients and therapists. In addition, the communication components enable remote assessments for clinical trials. An issue that plagues many clinical trials is obtaining outcome measures in a consistent manner. Variance in outcomes measurements can overshadow treatment effects. The disclosed system provides a solution to this issue by having only one, or by having only a small number, of raters perform assessments, centrally. This also allows only persons with high expertise to perform the assessments, thereby reducing variance due to many people of many skill levels doing outcomes assessments.

Some forms of rehabilitation therapy are best, or can only be, accomplished in a group setting, such as certain games that involve multiple players or patients, whether taking turns on a shared workstation, or when playing games on workstations connected by a network. Also, group interactions have social value that impact psychological aspects of disability, including psychological aspects of motor dysfunction after stroke. Art therapy, chatrooms, and support groups are all potential examples of how the disclosed system may be used for multi-patient interactions. This type of interaction addresses key psychosocial issues important to patient recovery.

The system further can be used for vocational training. When desired, features of the system can be tailored to emphasize activities that are related to job training and re-entering of the market place.

A number of principles of rehabilitation and plasticity have been incorporated into the content of rehabilitation system, such as incorporation of motor imagery, motor observation, inclusion of bilateral movements, sensory stimulation prior to movement practice, incorporation of music, incorporation of meditation and confidence building, mirror therapy, modulation of attention to task, contextual interference, cueing, socialization, enriched environment, provision of feedback, and gameifying to increase enjoyment, motivation, and compliance.

The system can further be used to educate patients. The system maximizes patient engagement in their own care by providing information about their underlying disease. This helps improve overall health, for example, by prevention of secondary complications and by improving risk factor management. The system can also be used to educate therapists. For example, the system can be used to deliver education such as webinars to clinicians who use the system, for example, by experts from around the world. Education can further extend to caregivers. A patient's caregiver, such as their spouse, plays an important role in rehabilitation and recovery. This system can help educate or provide support for a caregiver.

The invention claimed is:

1. A portable patient workstation configured to facilitate in-home rehabilitation therapy of a patient, the workstation comprising:
   a network connection device;
   a processing device communicatively coupled to the network connection device;
   a tabletop console communicatively coupled to the processing device, the tabletop console comprising a mat and one or more user interface devices mounted to the mat, wherein the one or more user interface devices are communicatively coupled to the processing device and configured to receive inputs from the patient, wherein the one or more user interface devices include a first plurality of buttons positioned on the mat and spaced apart so as to define four corners of a rectangular space on a surface of the mat, and a second plurality of buttons adjacent to each other and arranged in two lateral rows positioned within the rectangular space, wherein the lateral rows are biased towards one edge of the rectangular space, wherein the lateral rows are curved so as to ergonomically receive the patient's fingertips, wherein the first plurality of buttons are larger in size than the second plurality of buttons, wherein the first plurality of buttons are adapted to illuminate; and a memory communicatively coupled to the processing device, the memory includes software that includes one or more interactive programs that, upon execution by the processing device, perform one or more rehabilitation activities that are based on assessment data identifying a health condition for the patient and played back on a monitor, the one or more rehabilitative activities being conducted in accordance with a rehabilitation regimen tailored for the patient, wherein the tabletop console receives inputs from the patient via the one or more user interface devices when the rehabilitative activities are being conducted by the patient; and one or more software programs that, upon execution by the processing device, collect and store data associated with activities conducted by the patient in response to playback of the one or more rehabilitative activities, the one or more software programs being further configured to transmit at least a portion of the stored data via the network connection device.

2. The patient workstation of claim 1, wherein the one or more interactive programs are configured to adjust a metric of the one or more rehabilitative activities in real-time in response to input from the patient, the metric includes a difficulty level of the one or more rehabilitative activities.

3. The patient workstation of claim 2, wherein the assessment data including scores associated with a Fugl-Meyer assessment for the patient.

4. The patient workstation of claim 1, wherein the data associated with the activities conducted by the patient includes (i) times at which the patient uses the workstation, (ii) duration of time the patient uses the workstation, and (iii) the activities conducted by the patient using the workstation.

5. The patient workstation of claim 1, wherein the one or more user interface devices further include a rotatable dial.

6. The patient workstation of claim 1, further including auxiliary user interface devices separate from the console and receive the patient inputs while the patient is participating in the activities.

7. The patient workstation of claim 6, wherein the auxiliary user interface devices include a member including a force sensor configured to measure the force with which the member is squeezed or pinched by the patient.

8. The patient workstation of claim 1, further comprising a camera and a speaker communicatively coupled to the processing device and the network connection device to establish a video conference session to a network server accessible by a physical therapist while the patient participates in the activities.

9. A method for facilitating in-home rehabilitation therapy, the method comprising:

inputting parameters indicative of a physical or mental impairment of a patient into a computer, the parameters include Fugl-Meyer scores;

responsive to receiving the input parameters, executing an algorithm that recommends computer-based activities that can be prescribed to the patient to address the patient's particular physical or mental impairment based on the Fugl-Meyer scores assigned to each of the input parameters, the computer-based activities being automatically generated and displayed for acceptance by a therapist or substitution of at least one rehabilitative activity with an activity selected by the therapist to produce a rehabilitation itinerary to form a rehabilitation regimen of a plurality of rehabilitative activities tailored for the patient;

providing a patient workstation having a tabletop console comprising a mat and one or more user interface devices mounted to the mat, wherein the one or more user interface devices include a first plurality of buttons positioned on the mat and spaced apart so as to define four corners of a rectangular space on a surface of the mat, and a second plurality of buttons adjacent to each other and arranged in two lateral rows positioned within the rectangular space, wherein the lateral rows are biased towards one edge of the rectangular space, wherein the lateral rows are curved so as to ergonomically receive the patient's fingertips, wherein the first plurality of buttons are larger in size than the second plurality of buttons, wherein the first plurality of buttons are adapted to illuminate; and programming the patient workstation to host a selected plurality of the computer-based activities for the patient, wherein the tabletop console is configured to receive inputs from the patient via the one or more user interface devices when the activities are being performed by the patient.

10. The method of claim 9, wherein the forming of the rehabilitation regimen further includes selecting a duration for which each of the plurality of rehabilitation activities is to be performed and a number and duration of breaks during each of the plurality of rehabilitation activities.

11. The method of claim 9, wherein the computer-based activities include interactive computer games that the patient can play using user interface devices of the patient workstation.

12. The method of claim 9, further comprising collecting and storing data associated with the patient's participation in the computer-based activities and using the data to evaluate the patient's rehabilitation progress and to modify the plurality of the computer-based activities based on the patient's rehabilitation progress.

13. A rehabilitation system for facilitating in-home rehabilitation therapy of a patient, said system comprising:

a. a therapist control system that tracks and analyzes data to evaluate patient performance of rehabilitative exercises, comprising:

a therapist network connection device;

a therapist processing device communicatively coupled to the therapist network connection device; and a therapist memory communicatively coupled to the therapist processing device, the therapist memory includes software that includes:

a first therapist software program that, upon execution by the therapist processing device, receives assessment data identifying a health condition for the patient, and automatically generates one or more potential rehabilitative activities based on the assessment data, the one or more potential rehabilitative activities being displayed for acceptance by a therapist or substitution of at least one rehabilitative activity with an activity selected by the therapist to produce a rehabilitation itinerary to form a rehabilitation regimen of a plurality of rehabilitative activities tailored for the patient; and a second therapist software program that, upon execution by the therapist processing device, analyzes data associated with activities conducted by the patient performing the plurality of rehabilitative activities and generates revised rehabilitative activities based on the analyzed data for transmission to a patient workstation; and b. the patient workstation including:

a patient network connection device;

a patient processing device communicatively coupled to the patient network connection device;

a tabletop console communicatively coupled to the patient processing device, the tabletop console comprising a mat and one or more user interface devices mounted to the mat, wherein the one or more user interface devices are communicatively coupled to the patient processing device and configured to receive inputs from the patient, wherein the one or more user interface devices include a first plurality of buttons positioned on the mat and spaced apart so as to define four corners of a rectangular space on a surface of the mat, and a second plurality of buttons adjacent to each other and arranged in two lateral rows positioned within the rectangular space, wherein the lateral rows are biased towards one edge of the rectangular space, wherein the lateral rows are curved so as to ergonomically receive the patient's fingertips, wherein the first plurality of buttons are larger in size than the second plurality of buttons, wherein the first plurality of buttons are adapted to illuminate; and a patient memory communicatively coupled to the patient processing device, the patient memory includes software that includes one or more patient interactive programs that, upon execution by the patient processing device, perform one or more of the plurality of rehabilitative activities that are tailored for the patient and played back on a monitor, the one or more rehabilitative activities being conducted in accordance with the rehabilitation regimen, wherein the tabletop console receives inputs from the patient via the one or more user interface devices when the rehabilitative activities are being conducted by the patient; and one or more patient software programs that, upon execution by the patient processing device, collect and store data associated with activities conducted by the patient in response to playback of the one or more rehabilitative activities, the one or more software programs being further configured to transmit at least a portion of the stored data via the patient network connection device to the therapist control system.

14. The rehabilitation system of claim 13, wherein the assessment data includes scores associated with a Fugl-Meyer assessment for the patient.

15. The rehabilitation system of claim 13, wherein the producing of the rehabilitation itinerary to form the rehabilitation regimen including a plurality of rehabilitative activities includes selecting a duration for which each of the plurality of rehabilitation activities is to be performed and a number and duration of breaks during each of the plurality of rehabilitation activities.

16. The rehabilitation system of claim 13, wherein the scores are processed by at least the first software program to generate the therapy recommendations.

17. The rehabilitation system of claim 13, wherein the one or more patient interactive programs are configured to adjust a metric of the one or more rehabilitative activities in real-time in response to input from the patient, the metric includes a difficulty level of the one or more rehabilitative activities.

18. The rehabilitation system of claim 13, wherein the data associated with the activities conducted by the patient includes (i) times at which the patient uses the workstation, (ii) duration of time the patient uses the workstation, and (iii) the activities conducted by the patient using the workstation.

19. The rehabilitation system of claim 13, wherein the patient workstation further comprises auxiliary user interface devices separate from the console and receive the patient inputs while the patient is participating in the activities.

20. The rehabilitation system of claim 19, wherein the auxiliary user interface devices include a member including a force sensor configured to measure the force with which the member is squeezed or pinched by the patient.

* * * * *